US006440940B1

(12) United States Patent
Doyle et al.

(10) Patent No.: US 6,440,940 B1
(45) Date of Patent: *Aug. 27, 2002

(54) BIORESORBABLE ALGINATE DERIVATIVES

(76) Inventors: Peter J. Doyle, 22, The Cleaves, Tullibody, Clackmannanshire FK10 2XD (GB); Wilson Harvey, 23, The Glebe Gargunnock, Stirling FK8 3AX (GB); Reginald L. Stilwell, 600 Oakland Hills Dr., Arlington, TX (US) 76018

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/993,372

(22) Filed: Dec. 18, 1997

(51) Int. Cl.[7] ........................ A61K 31/715; C08B 37/04
(52) U.S. Cl. .............. 514/23; 514/54; 536/3; 424/445
(58) Field of Search ............... 514/23, 54; 536/3; 424/445

(56) References Cited

U.S. PATENT DOCUMENTS

| 3,523,027 A | | 8/1970 | Hall ......................... 99/176 |
| 3,702,843 A | * | 11/1972 | Schweiger ................. 260/91.3 |
| 3,784,475 A | | 1/1974 | Diehl .......................... 252/89 |
| 3,900,425 A | | 8/1975 | Robinson .................... 252/430 |
| 4,016,098 A | | 4/1977 | Saeki et al. ................. 252/316 |
| 5,470,576 A | * | 11/1995 | Patel ......................... 424/445 |
| 5,714,232 A | * | 2/1998 | Fenton et al. ............... 428/171 |
| 5,718,916 A | * | 2/1998 | Scherr ....................... 424/445 |

FOREIGN PATENT DOCUMENTS

| EP | 693291 | 7/1995 |
| EP | 815879 | 6/1997 |
| EP | 0842981 | 6/1998 |
| GB | 1109509 | 9/1965 |
| GB | 1250516 | 4/1969 |
| GB | 1295666 | 6/1969 |
| GB | 1436700 | 5/1972 |
| GB | 1488396 | 12/1974 |
| WO | 96/03439 | 8/1993 |
| WO | 93/16110 | 2/1996 |

OTHER PUBLICATIONS

The Carbohydrates—Chemistry and Biochemistry (2nd Edition) vol. IIB, edited by Pigman and Horton, publ. by Academic Press, pp. 545–550, 1970.*
Smidsrod et al. "Chemistry and physical properties of alginates", Carbohydrates in Europe, pp. 6–13, May 1996.*
*The Carbohydrates,* ed. by Ward Pigman, publ. by Academic Press Inc., pp. 696–701, (1957).*
*Chemistry of the Carbohydrates,* ed. by Pigman & Goepp, publ. by Academic Press Inc., pp. 614–618, 1948.*
European Search Report No. 97310395.5–2115 dated Mar. 27, 1998.
XP002059181 Derwent Publications Ltd., London, GB:AN 75–33302W, Abstract, Feb. 21, 1975.
Great Britain Search Report No. GB 9626466.8 dated Mar. 5, 1997.
English Abstract: WO 93/16110 Publication Date: Aug. 19, 1993.
English Abstract: WO 96/03439 Feb. 1, 1996.
Austrian Patent Office: Written Opinion, Application Number 9704497.8, dated Dec. 30, 1998.

* cited by examiner

*Primary Examiner*—Ralph Gitomer
*Assistant Examiner*—Devesh Khare
(74) *Attorney, Agent, or Firm*—Andrew C. Farmer; Theodore J. Shatynski

(57) ABSTRACT

The invention provides oxidized alginates that are bioresorbable. The oxidized alginates are prepared by controlled oxidation of alginates with nitrogen tetroxide or the like, The invention also provides pharmaceutical compositions, wound dressings, surgical implants and prostheses comprising the oxidized alginate derivatives.

20 Claims, 3 Drawing Sheets

D-MANNURONIC ACID

L-GULURONIC ACID

D-MANNURONIC ACID

L-GULURONIC ACID

BIORESORBABLE ALGINATE DERIVATIVES

BACKGROUND

The present invention relates to bioresorbable alginate derivatives and processes for the production thereof. The present invention also relates to the use of such bioresorbable alginate derivatives in pharmaceutical compositions, especially wound dressings, implants and surgical prostheses.

Alginates are linear binary copolymers of D-mannuronic acid (MA) and L-guluronic acid (CA) having the structures shown in FIG. 1. The polymers are built up by ether linkages joining the 1- and 4- positions of the MA and GA saccharide residues. Alginates are isolated from marine brown algae, and such naturally occurring alginates generally comprise blocks of MA rich units. GA rich units and mixed sequences of MA and GA units. Commercially available alginates of this type typically contain about 45% of MA.

Alginates are available in the form of alginic acid, various salts, and various ester derivatives such as propyleneglycol alginates. Alginate salts with monovalent cations such as sodium are generally soluble in water. Alginate salts formed with divalent or trivalent cations such as calcium or zinc are generally insoluble in water. The solubility of alginate compositions can thus be controlled over a wide range by varying the sodium/calcium ratio of mixed sodium/calcium alginate salt. Commercially available alginate products are generally formed from such mixed salts.

Alginate products have long been used in the field of wound healing, especially as a packing material for cavity wounds or for treatment of burns. Alginate materials are sold under the registered trade marks KALTOSTAT (Britcaire Limited), SORBSAN (Pharma-Plast Limited) and ALGOSTERIL (Johnson & Johnson). These products are available in a number of forms, including ropes and pads. These materials are highly absorbent, biocompatible and cheap.

Although alginates have good properties for treating cavity wounds and burns, care has to be taken when changing the dressings to ensure that nothing is left in the wound. Alginate is not bioresorbable, but does tend to fragment. If left in the wound, fragments of alginate will result in the formation of granulomas. It is therefore necessary to rinse the wound out thoroughly with saline solution to ensure that no residual alginate remains.

Alginates have also been shown to have excellent haemostatic properties, but because they are not resorbable they must be removed prior to closure of a wound, which inevitably limits their usefulness in this application.

Accordingly, there exists a need for improved materials, in particular for wound dressing and haemostatic applications, that exhibit the advantages of alginates and are also bioresorbable.

It has long been known that cellulose can be rendered bioresorbable by exposure to an oxidizing agent such as dinitrogen tetroxide, as described in U.S. Pat. No. 3,122,479. The resulting oxidized regenerated cellulose (ORC) is available in the form of a knitted fabric under the registered trade mark SURGICEL for use as an absorbable haemostat. ORC is also available under the registered trade mark INTERCEED for use as an adhesion barrier. The bioresorbable character of ORC is thought to be due to oxidation of the primary hydroxyl groups on the cellulose residues to carboxylate groups.

U.S. Pat. No. 4,543,410 describes absorbent, coherent, flexible structures in the form of fibrous webs and porous sponges comprising water-insoluble, ring oxidized cellulosic bases. It is stated that ring oxidation of the cellulosic bases can selectively convert the hydroxyl groups at the 2, 3 and 6 positions of the anhydroglucose units of cellulose into carboxyl groups, depending on the specific oxidant used. It is stated that dinitrogen tetroxide converts the hydroxyl group at the 6 position into a carboxyl group to product a mono-carboxyl form of the base (as in the formation of ORC). Periodic acid will open the ring between the 2 and 3 position and convert the hydroxyl groups at the 2 and 3 position into aldehyde groups. The resulting dioxide can be further oxidized with chlorine or dinitrogen tetroxide to product a dicarboxyl or tricarboxyl form of the base. It is stated that ring oxidized cellulosic base sponges having a carboxyl content due to ring oxidation greater than about 15% are haemostatic and bioresorbable. Ring oxidation of starch is also disclosed.

SUMMARY OF THE INVENTION

It has now been found that ring oxidation of alginates with oxidizing agents such as dinitrogen tetroxide results in bioresorbable, oxidized alginate derivatives. This result is surprising, since the saccharide residues making up the alginate molecules are already fully oxidized to carboxylate at the 6 position before treatment with the dinitrogen tetroxide.

Accordingly, the present invention provides an oxidized alginate.

Preferably, at least part of the MA and/or GA saccharide residues of the alginate have been oxidized at the 2- or 3- position. Such oxidation could take place without ring opening, by oxidation of the secondary alcohol groups to keto groups, or it can take place with ring opening to dialdehyde or dicarboxylate derivatives. More preferably, at least 0.2% of the saccharide residues of the alginate have been oxidized at the 2- or 3- position, and still more preferably at least 1.0% of the saccharide residues have been so oxidized.

Preferably, the ring oxidation of the alginate residues has taken place with ring opening to dicarboxylic acid derivatives. As a result, the oxidized alginate according to the present invention preferably has a carboxylate content greater than that of the starting alginic acid. Preferably, the carboxylate content is increased by at least 1%, and more preferably there is at least 2% increase in the number of carboxylate groups relative to the corresponding unoxidized material. The carboxylate content is determined as follows:

A sample of oxidized alginate (approximately 0.2 g) is dissolved in 0.5M sodium hydroxide (5 ml) and a couple of drops of 0.1% phenolphthalein indicator solution are added. The excess sodium hydroxide is back-titrated with 0.1M HCl to the phenolphthalein end point (red to clear). A blank value is determined by titrating 5 ml 0.1M sodium hydroxide with 0.1M HCl. The value for carboxyl content (percentage by weight) is calculated using the equation:

$$C = \frac{4.5 \times (B-S) \times M}{W}$$

wherein:
C=percent carboxyl content
B=volume of standard HCl to titrate blank (ml)
S=volume of standard HCl to titrate sample (ml)
M=molality of standard HCl
M=dry weight of sample (g)
(4.5=milliequivalent weight of carboxyl×100)

The oxidized alginate is more bioabsorbable and bioassimilable in the mammalian body. Preferably, the oxidized alginate is fully absorbable when implanted in the mammalian body.

The oxidized alginate derivatives according to the present invention have substantially similar solubility behaviour to naturally occurring alginates. In particular, the solubility of oxidized alginate salts can be varied by varying the ratio of sodium and calcium cations. Preferably, the oxidized alginates according to the present invention are substantially insoluble in water. This implies that the oxidized alginates according to the present invention is preferably a salt of the oxidized alginate and divalent of trivalent cations, such as calcium or zinc ions.

Preferably, the oxidized alginates according to the present invention have a weight average molecular weight in the range 10,000 to 1,000,000, more preferably 50,000 to 400,000.

The present invention also provides a pharmaceutical composition comprising an oxidized alginate according to the invention. The invention also provides a wound dressing, surgical implant or prosthesis comprising an oxidized alginate according to the invention, and the use of such an oxidized alginate for the preparation of a wound dressing, surgical implant or prosthesis.

In another aspect, the present invention provides a method of treating a wound in a mammalian body, comprising applying to the wound a wound dressing comprising an oxidized alginate as hereinbefore defined.

In another aspect, the present invention provides a process to prepare an oxidized alginate comprising the steps of: contacting an alginate with an oxidizing agent to oxidize the alginate; followed by isolating and washing the oxidized alginate. Preferably, the oxidizing agent comprises dinitrogen tetroxide in an inert solvent. However, other oxidizing agents such as chlorine, ozone or periodic acid may be used. Preferably, the alginate is solid before, during and after the contacting step. For example, the starting alginate may be a calcium alginate foam, web or fleece.

DETAILED DESCRIPTION

Specific embodiments of the present invention will now be described further, by way of example, with reference to the accompanying drawings, in which.

EXAMPLE 1

An oxidized alginic acid derivative according to the present invention was prepared as follows.

20 grams of alginic acid (Sigma Chemical Company) was suspended in 150 grams of fluorocarbon solvent (solvent FC77 supplied by 3M Corporation). 20 grams of liquid dinitrogen tetroxide was dissolved carefully in 50 grams of the same fluorinated solvent and slowly added to the alginate suspended over 2 hours at room temperature. The mixture was left to react at room temperature for a further 4 hours. The resulting slurry was decanted into a Buchner funnel fitted with a porous glass frit, and the oxidized alginate was collected. The oxidized alginic acid was washed by reslurrying in fluorocarbon solvent for 10 minutes and collected by Buchner filtration. The oxidized alginic acid was then washed 4 times in 90% isopropanol and twice in 100% isopropanol before being allowed to dry in air.

The oxidized alginic acid was converted to its sodium salt by reacting with 12 grams of sodium acetate dissolved in 200 ml distilled water. The sodium salt of the oxidized alginic acid was reprecipitated as the calcium salt by adding an excess of calcium chloride to the oxidized sodium alginate solution. The calcium alginate was collected by centrifugation, washed extensively in distilled water, and air dried.

The resulting material is an off-white powder that is soluble in 0.5 molar sodium hydroxide solution.

EXAMPLE 2

The breakdown of the oxidized alginic acid prepared in Example 1 on incubation in serum is studies as follows.

A sample of oxidized alginic acid prepared and described in Example 1 was added to serum at a concentration of 10 mg/ml, and the pH was readjusted to 7.4 using 0.5M NaOH. The dispersion was then incubated at 37° C. for 48 hours. Following incubation, the sample was passed through a 0.2 $\mu$m filter. A 10 ml sample of the filtrate solution was then injected into a Dionex (registered trade mark) 500 ion-exchange chromatography system fitted with a Carbopac VA 1 an ion exchange column (25 cm×4 mm) with Carbopac PA 1 guard column (5 cm×4 mm). The mobile phase was as follows: eluent A-ultrapure water; eluent B—200 mN sodium hydroxide; and eluent C—2 M sodium acetate.

The solution gradient programme was as follows:

initial-100% B; 0–20 minutes—86% A, 10% B, 4% C; 20–70 minutes—from 86% A, 10% B, 4% C to 40% A, 10% B, 50% C; 70–80 minutes—100% B.

The sample was injected 15 minutes into the run, and data was collected from the moment the sample was injected until the end of the run.

Figure 1:
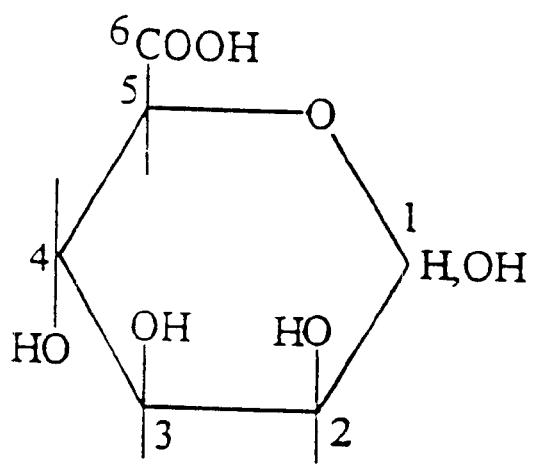
FIG. 1 shows the structures of the mannuronic acid and gulronic acid building blocks of alginate prior to oxidation.
Figure 1:
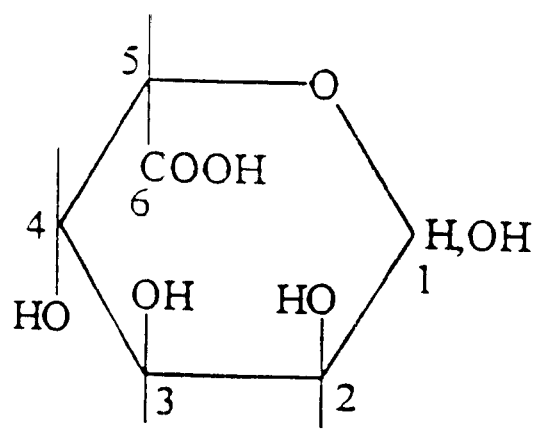
Figure 2:
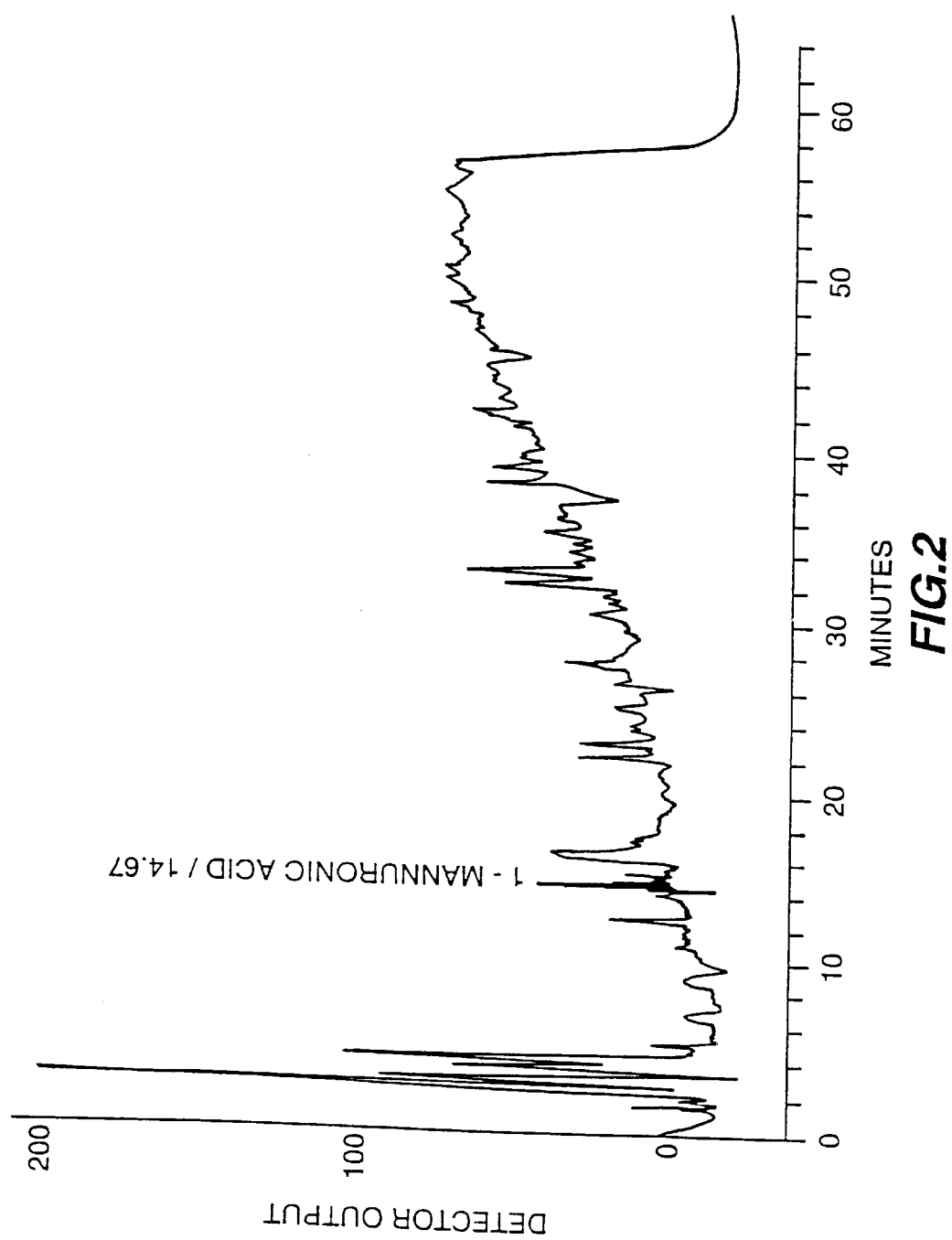
FIG. 2 shows an ion-exchanged chromatogram of breakdown products of oxidized alginic acid incubated in serum for 48 hours.

The chromatogram shown in FIG. 2 exibits a number of elution peaks between 10 minutes and 50 minutes, corresponding to the various fragments of the oxidized alginic acid that has undergone breakdown in the serum. The peak corresponding to mannuronic acid (identified in a comparative run with added pure mannuronic acid) is marked.

This example illustrates that oxidized alginic acid undergoes breakdown into a number of soluble components in serum at 37° C.

EXAMPLE 3 (Comparative)

Figure 3:
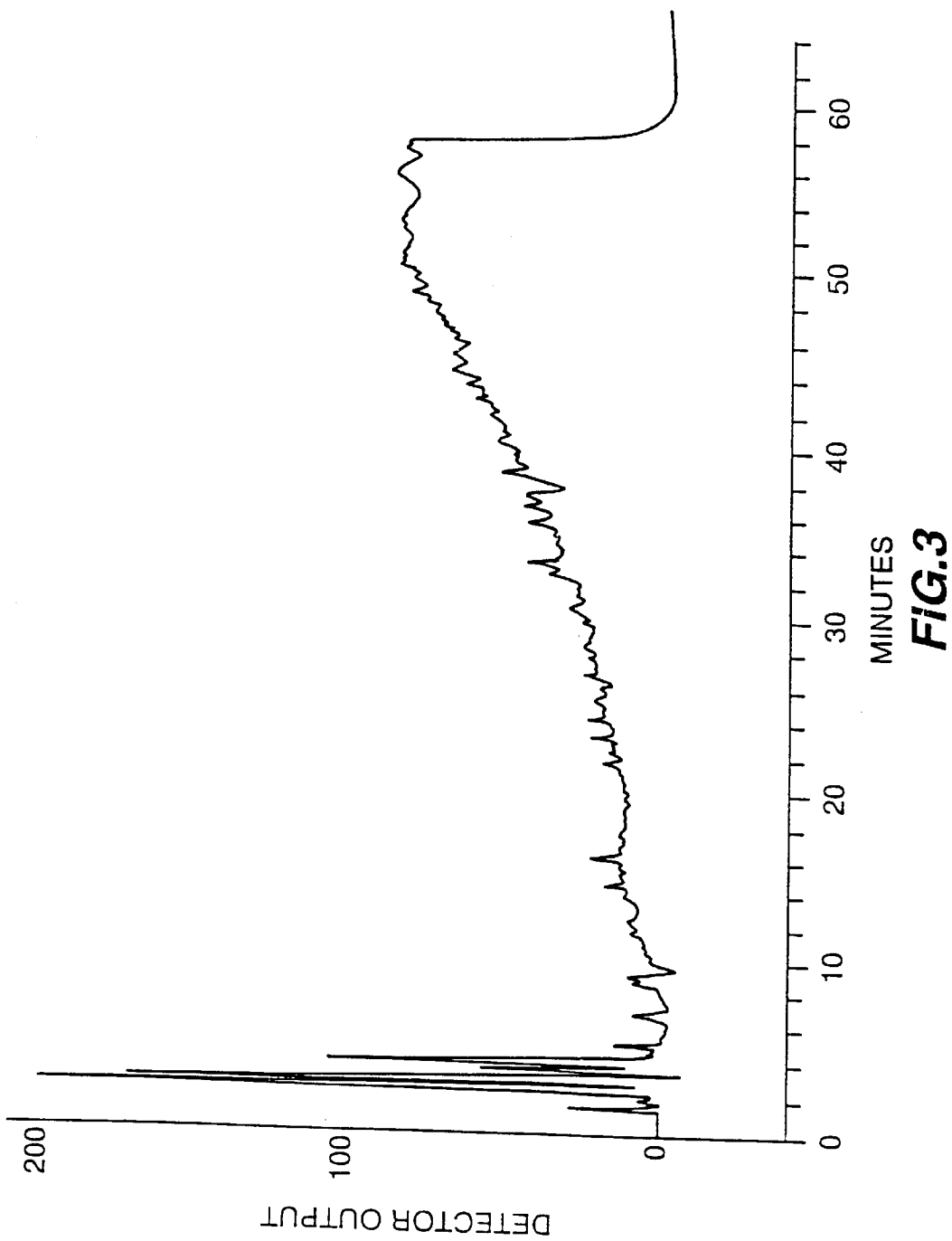
FIG. 3 shows a comparative ion-exchange chromatogram of unoxidized alginic acid incubated in serum for 48 hours.

The experimental procedure of Example 2 was repeated exactly with unoxidized alginic acid in place of the oxidized alginic acid. The resulting chromatogram is shown in FIG. 3. It can be seen that the chromatogram for alginic acid is substantially free of elution peaks for breakdown products observed for the oxidized alginic acid. This accords with clinical observations that unoxidized alginates do not undergo breakdown into soluble components in vivo.

EXAMPLE 4

Samples of oxidized alginic acid were prepared as described in Example 1, but with varying oxidation times in the dimitrogen tetroxide solution. The carboxylate content of the oxidized alginic acids was then determined by titration, as described above. The results were as follows:

| Oxidation Time (hrs) | Carboxylate Content (wt. %) |
| --- | --- |
| 0 (comparative) | 23.12 |
| 2 | 23.15 |
| 4 | 23.51 |
| 20 | 24.90 |
| 72 | 27.25 |

It can thus be seen that the extent of oxidation to form new carboxylate groups increases with time. It can also be seen that relatively few additional carboxylate groups, e.g. about 1.5% based on the original carboxylate groups, are needed to produce the bioabsorbable alginate after four hours.

EXAMPLE 5

The properties of oxidized alginic acid prepared as described in Example 1 were studied by thermogravimetry and differential scanning calorimetry (DSC) in air from 30° C. to 200° C. at 10° C. per minute. The TGA results were as follows:

| Oxidation Time (hrs) | Weight Loss (%) |
| --- | --- |
| 0 (comparative) | 16.98% |
| 20 | 25.09% |
| 72 | 38.31% |

In addition, the oxidized samples showed a marked endotherm above 100° C. and changed colour to black.

The above embodiments have been described by way of example only. Many other embodiments falling within the scope of the accompanying claims will be apparent to the skilled reader.

EXAMPLE 6

The properties of oxidised alginate in vivo were studied as follows:
(1) Preparation of Comparative Alginate Pads.

Calcium alginate (0.5 g) and sodium alginate (1 g) were homogenised in 100 ml distilled water and poured into a 10 cm×10 cm petri dish. The solution was frozen, freeze dried and the resultant pad cut into 1×0.5 cm blocks. These were γ-irradiation sterilised.
(2) Preparation of Oxidised Alginate Pads.

Oxidised calcium alginate (0.5 g) and oxidised sodium alginate (1 g) prepared as described in Example 1 were homogenized in 100 ml distilled water and poured into a 10 cm×10 cm petri dish. The solution was frozen, freeze dried and the resultant pad cut into 1×0.5 cm blocks. There were γ-irradiation sterilised.
(3) In Vivo study Twelve Sprague Dawley rats were used in the study. Under standard operating conditions, two pads of each material were subcutaneously implanted on the ventral surface of each rat. Four rats were sacrificed on 3, 7 and 14 days post-implantation. The alginate pads were removed at that time complete with the overlying dermis and the underlying musculature. The samples were fixed in formaldehyde and processed for routine history. Sections of the alginate pads were made from as close to the centre of the pads as possible. These were stained with either H&E or Masson's Trichrome and examined under a light microscope. The number of neutrophils present in each section was used as an indicator of the intensity of the inflammatory reaction.

The oxidised alginate pads were found to resorb at a faster rate than those prepared from normal alginate. The oxidised alginate pads were also found to elicit a reduced inflammatory response when composed to the normal material.

What is claimed is:

1. An oxidized alginate which is substantially insoluble in water and bioresorbable.

2. An oxidized alginate according to claim 1, wherein at least part of the saccharide residues of the alginate have been oxidized at the 2- or 3- position.

3. An oxidized alginate according to claim 2, wherein at least 0.1% of the saccharide residues of the alginate have been oxidized at the 2- or 3- position.

4. An oxidized alginate according to claim 3, wherein at least 1.0% of the saccharide residues of the alginate have been oxidized at the 2- or 3- position.

5. An oxidized alginate according to claim 1, wherein said oxidation has taken place with ring opening.

6. An oxidized alginate according to claim 1, wherein the carboxylate content is increased by at least 1% relative to a corresponding unoxidized alginate.

7. An oxidized alginate according to claim 1 which is fully absorbable when implanted in a mammalian body.

8. An oxidized alginate according to claim 1 having a weight average molecular weight in the range 10,000 to 1,000,000.

9. A pharmaceutical composition comprising an oxidized alginate according to claim 1.

10. A wound dressing, surgical implant or prosthesis comprising an oxidized alginate according to claim 1.

11. An oxidized alginate according to claim 1 which comprises an oxidized alginate salt of calcium.

12. An oxidized alginate according to claim 1 which comprises an oxidized alginate salt of sodium reprecipitated as the calcium salt thereof. comprising an oxidized alginate according to claim 1.

13. A process to prepare an oxidized alginate comprising the steps of:

contacting an alginate with an oxidizing agent;

forming a salt of the alginate with divalent or trivalent cations;

thereby forming an oxidized alginate which is bioresorbable and insoluble in water;

followed by isolating and washing the oxidized alginate.

14. A process according to claim 13, wherein the oxidizing agent comprises $N_2O_4$ in an inert solvent.

15. A process according to claim 13, wherein the alginate is solid before, during and after said contacting step.

16. A wound dressing comprising a pad which comprises an oxidized alginate which is bioresorbable.

17. A wound dressing according to claim 16 wherein the oxidized alginate is substantially insoluble in water.

18. A wound dressing according to claim 17 wherein the oxidized alginate comprises an oxidized alginate salt of calcium.

19. A wound dressing according to claim 17 wherein the oxidized alginate comprises an oxidized alginate salt of sodium reprecipitated as the calcium salt thereof.

20. A wound dressing according to claim 17 comprising a pad which comprises the oxidized alginate and which is freeze dried.

* * * * *